(12) United States Patent
Brown

(10) Patent No.: US 8,409,173 B2
(45) Date of Patent: Apr. 2, 2013

(54) HOLDING DEVICE FOR MEDICAL PURPOSES

(75) Inventor: Stuart I. Brown, St. Andrews (GB)

(73) Assignee: University of Dundee (GB)

( * ) Notice: Subject to any disclaimer, the term of this patent is extended or adjusted under 35 U.S.C. 154(b) by 1139 days.

(21) Appl. No.: 12/030,398

(22) Filed: Feb. 13, 2008

(65) Prior Publication Data
US 2008/0194909 A1    Aug. 14, 2008

(30) Foreign Application Priority Data

Feb. 13, 2007 (DE) .......................... 10 2007 006 891

(51) Int. Cl.
A61B 17/00    (2006.01)
A61B 1/00    (2006.01)
A61B 19/00    (2006.01)

(52) U.S. Cl. .............................. 606/1; 600/102; 606/130

(58) Field of Classification Search .......... 600/102–104, 600/117, 118; 606/130, 1
See application file for complete search history.

(56) References Cited

U.S. PATENT DOCUMENTS

| | | | | |
|---|---|---|---|---|
| 5,441,042 A * | 8/1995 | Putman | .......................... | 600/102 |
| 5,609,565 A * | 3/1997 | Nakamura | ..................... | 600/229 |
| 5,779,623 A * | 7/1998 | Bonnell | ......................... | 600/114 |
| 5,796,183 A * | 8/1998 | Hourmand | ..................... | 307/116 |
| 5,876,325 A | 3/1999 | Mizuno et al. | ................. | 600/102 |
| 5,888,190 A * | 3/1999 | Meyer et al. | ..................... | 600/102 |
| 5,971,976 A * | 10/1999 | Wang et al. | ........................ | 606/1 |
| 6,106,511 A * | 8/2000 | Jensen | ................................ | 606/1 |
| 6,120,433 A * | 9/2000 | Mizuno et al. | ................. | 600/102 |
| 6,471,165 B2 * | 10/2002 | Twisselmann | ............ | 248/123.11 |
| 6,514,239 B2 * | 2/2003 | Shimmura et al. | ................. | 606/1 |
| 6,569,084 B1 * | 5/2003 | Mizuno et al. | ................. | 600/102 |
| 6,587,750 B2 * | 7/2003 | Gerbi et al. | ..................... | 700/245 |
| 6,632,170 B1 * | 10/2003 | Bohanan et al. | .............. | 600/102 |
| 6,999,852 B2 * | 2/2006 | Green | ............................ | 700/245 |
| 7,189,246 B2 * | 3/2007 | Otsuka et al. | .................. | 606/130 |
| 7,192,396 B2 * | 3/2007 | Boulais | .......................... | 600/118 |

(Continued)

FOREIGN PATENT DOCUMENTS

DE    195 26 915    2/1997
EP    0017318 A1    10/1980

(Continued)

OTHER PUBLICATIONS

German Search Report, Sep. 14, 2007, 4 pages.

(Continued)

Primary Examiner — Philip R Smith
Assistant Examiner — William Chou
(74) Attorney, Agent, or Firm — St. Onge Steward Johnston & Reens LLC

(57) ABSTRACT

The invention relates to a holding device for medical purposes having a carrier arm on whose distal end at least one medical instrument can be secured and having at least one joint for positioning the carrier arm and/or the medical instrument, wherein the at least one joint can be transferred between a position that releases the joint and a position that blocks the joint and wherein the at least one joint is coupled with a touch sensor for actuating the joint. To produce a holding device for medical purposes that ensures simple construction, simple handling, and reliable positionability, it is proposed with the invention that the sensor should be coupled with the medical instrument mounted on the distal end of the carrier arm.

1 Claim, 1 Drawing Sheet

U.S. PATENT DOCUMENTS

| | | | | |
|---|---|---|---|---|
| 7,837,599 B2* | 11/2010 | Kowalczewski et al. | ....... | 482/44 |
| 7,841,979 B2* | 11/2010 | Hirose | .......... | 600/102 |
| 2002/0177857 A1* | 11/2002 | Otsuka et al. | ................. | 606/130 |
| 2003/0176948 A1* | 9/2003 | Green | .......................... | 700/264 |
| 2004/0186345 A1* | 9/2004 | Yang et al. | ................... | 600/102 |
| 2004/0267089 A1* | 12/2004 | Otsuka et al. | ................. | 600/102 |
| 2005/0165271 A1* | 7/2005 | Shioda et al. | ................. | 600/102 |
| 2005/0256371 A1* | 11/2005 | Schara et al. | ................. | 600/102 |
| 2010/0087835 A1* | 4/2010 | Blumenkranz et al. | ....... | 606/130 |

FOREIGN PATENT DOCUMENTS

| | | |
|---|---|---|
| EP | 11 52 182 | 11/2001 |
| EP | 1557134 A1 | 7/2005 |
| WO | 2007005976 A1 | 1/2007 |

OTHER PUBLICATIONS

European Search Report, EP08001874, Jun. 9, 2008, 6 pages.

* cited by examiner

HOLDING DEVICE FOR MEDICAL PURPOSES

CROSS-REFERENCE TO RELATED APPLICATIONS

The present application claims priority of German patent application No. 10 2007 006 891.5 filed on Feb. 13, 2007, the content of which is incorporated herein by reference.

FIELD OF THE INVENTION

The invention relates to a holding device for medical purposes having a carrier arm on whose distal end at least one medical instrument can be secured and having at least one joint for positioning the carrier arm and/or the medical instrument, wherein the at least one joint can be displaced between a position that releases the joint and a position that blocks the joint and wherein the at least one joint is coupled with a touch sensor for actuating the joint.

BACKGROUND OF THE INVENTION

Holding devices of this type are frequently required in performing surgical interventions in order to hold medical instruments of various types, such as retractors, video cameras, or endoscopes, in a particular position for an extended period. Owing to the jointed design of the holding devices, it is possible for the surgeon to position with exactitude the medical instrument that is held in the instrument intake and, by blocking the joint or joints, to fix the position of the holding device that has been selected.

A generic holding device is known for instance from U.S. Pat. No. 6,587,750 B2. This known device is a remote-controlled surgical robotic device the handle of which can be actuated by a touch sensor. The disadvantage of this known construction is that positioning errors in the area of the medical instrument can occur, especially with long and multipartite carrier arms, if mere touching of the handle immediately converts the holding device into a movable position.

An additional holding device is known, for instance, from DE 195 26 915 B4. With this known holding device, the joint parts are blocked with respect to one another by friction locking owing to the spring force of at least one spring element. Releasing the blocking occurs pneumatically by means of blades positioned in the joint, which when impacted for instance by compressed air can ensure separation of the friction lock. Although holding devices of this type have proven themselves in the art, it is precisely the contact surfaces that are to be held together by the friction lock which constitute problems in cleaning because, with the high contact forces that are required to produce a reliable friction lock, scratches can be caused in the contact surface which in turn can form germ cells for impurities.

SUMMARY OF THE INVENTION

Consequently it is the object of the invention to produce a holding device for medical purposes which is of simple construction, is simple to operate, and ensures reliable positionability.

The fulfillment of this object according to the invention is characterized in that the sensor is coupled with the medical instrument that is positioned on the distal end of the carrier arm.

Through the inventive coupling of the sensor with the medical instrument that is positioned on the distal end of the carrier arm so that the sensor is advantageously switched in such a way that the at least one joint can be converted into the position that releases the joint by means of actuation of the sensor, it is possible in a simple way for the operator to release the joint or joints only when he or she touches the medical instrument and thus can exert direct influence on the positioning of the medical instrument.

Without the assistance of a tool or other direct craftlike activity on the joint, such as the release or unscrewing. According to a practical embodiment of the invention, it is proposed that the touch sensor should be coupled with the medical instrument mounted on the distal end of the carrier arm. This inventive configuration has the advantage that the joint is automatically released at the moment when the operator touches the medical instrument that is to be used. Thus the operator can use the instrument directly and without any further activity at all and convert it into the desired new position. As soon as the operator releases the medical instrument again, the touch sensor is again deactivated and the joint is moved back into the position that blocks the joint, so that the medical instrument remains fixed in the position now adopted until the next release of the joint.

To facilitate the positionability of the medical instrument positioned on the distal end of the carrier arm, it is further proposed with the invention that the medical instrument positioned on the distal end of the carrier arm should be mounted in a movable instrument intake.

The instrument intake is likewise advantageously coupled with the inventive touch sensor, so that the operator with the gripping of the medical instrument can directly cause the complete release of the joint or joints of the carrier arm as well as of the instrument intake, in order to be able to convert the medical instrument into the best possible new working position directly and without additional help while taking advantage of all available degrees of freedom.

Finally, it is proposed with a practical embodiment of the invention that the sensor should be configured as a capacitive sensor. Alternatively, of course, it is also possible to configure the touch sensor as an inductive sensor for instance, or a temperature sensor or energy current sensor.

Further characteristics and advantages of the invention can be seen from the appended illustrations, in which an embodiment of an inventive holding device for medical purposes is schematically depicted exclusively in exemplary terms, without restricting the invention to this embodiment.

DETAILED DESCRIPTION OF THE INVENTION

Figure 1:
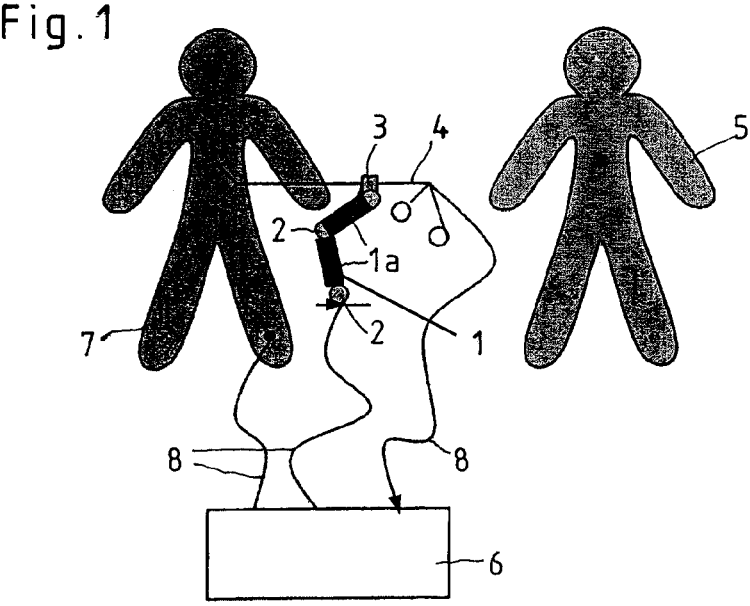
FIG. 1 shows a schematic view of an inventive holding device for medical purposes.

FIG. 1 shows schematically a holding device for medical instruments. This holding device consists essentially of a carrier arm 1 consisting of several carrier arm parts, such that the individual carrier arm parts 1a of the carrier arm 1 are connected with one another so that they can rotate relative to one another by means of the joint 2. In the area of its proximal end, the carrier arm 1 for instance can be secured on the operating table by means of a chucking device. On the distal end the carrier arm 1 comprises an instrument intake 3 for inserting a medical instrument 4 that is to be positioned by the holding device.

Holding devices of this type are frequently required in conducting surgical interventions in order to hold medical instruments 4 of various kinds, such as retractors, video cameras, or endoscopes, in a certain position for an extended period. Owing to the jointed configuration of the holding device, it is possible for the surgeon 5 to position the medical instrument 4 precisely and to secure the assumed position of the holding device by blocking the joint 2 or the joints 2. In addition to endoscopic surgery, holding devices of this type are used also in open surgery.

To be able to transfer the medical instrument 4 that is positioned on the distal end of the carrier arm 1 into a new working position, the joints 2 as well as the instrument intake 3 are configured in such a way that they can be transferred between a position that releases the movement and blocked position that fixes the carrier arm. In the illustrated embodiment, the joints 2 and the instrument intake 3 are coupled with a touch sensor 6 so that the sensor 6 in the current case is positioned on the medical instrument 4.

The touch sensor is configured in such a way that, as soon as the surgeon 5 grips the medical instrument 4 and thus also touches the sensor 6, the joints 2 and the instrument intake 3 are transferred into the position that releases the movement, so that the surgeon 5 can now transfer the medical instrument 4 into a new working position. As soon as the surgeon 5 releases the medical instrument 4 again and thus also is no longer touching the touch sensor 6, the joints 2 and the instrument intake 3 switch again into the blocking position in which the medical instrument 4 remains in the assumed position on the carrier arm 1.

In the illustrated embodiment, the touch sensor 6 is configured as a capacitive sensor, although it is also possible of course to configure the touch sensor 6 for instance as an inductive sensor, temperature sensor, or energy current sensor.

The functioning of the capacitive sensor 6 is based on the comparison of an undisturbed electric circuit with known electrical capacity with the electrical capacity of the electric circuit when the surgeon 5 touches the sensor 6 or the medical instrument 4 that is equipped with the sensor 6.

FIG. 1 schematically illustrates the structure of a holding device for medical instruments that is equipped with a capacitive sensor 6.

The medical instrument 4 is positioned in the instrument intake 3 on the distal end of the carrier arm 1 that can be moved by means of joints 2, in such a way that the joints 2 and the instrument intake 3 can be converted by directing an external force between a position that releases the movement of these components 2 and 3 and a position that blocks these components 2 and 3. The carrier arm itself is secured on the operating table by its proximal end, for instance by means of a chucking device. A patient 7 who is to be operated on, the carrier arm 1, and the medical instrument 4 are connected electrically by lines 8 with the capacity-sensitive electrical circuit. In addition this electrical circuit includes at least one outlet in order to monitor the joints 2 of the carrier arm 1 on the blocking or releasing position.

Alternatively to the illustrated embodiment, it is possible to dispense with the line 8 that connects the medical instrument 4 with the capacitor-sensitive electric current if the medical instrument 4 and the carrier arm 1 are of metallic construction. In this case the capacitive current runs through the medical instrument 4 and the carrier arm 1, so that the freedom of movement of the medical instrument 4 is clearly improved.

Figure 2:
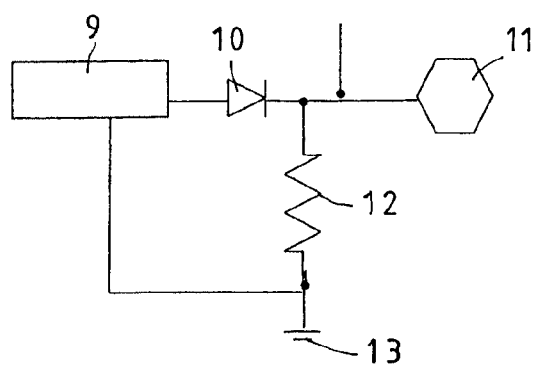
FIG. 2 shows a schematic electrical circuit diagram for a capacitive touch sensor.

The electric circuit of the holding device according to FIG. 1, which is schematically shown in FIG. 2, is configured in such a way that the joints 2 of the carrier arm 1 and the instrument intake 3 are held in the blocked position, in which the medical instrument 4 retains a position once assumed, if the surgeon 5 does not touch the medical instrument 4.

If the surgeon 5 wants to use the medical instrument 4 and to convert it into a different position, he grips the medical instrument 4. This gripping of the medical instrument 4 by the surgeon 5 is registered by the capacity-sensitive electric circuit because of the foreign capacity supplied to the system. This capacity modification causes the release of the joints 2 and of the instrument intake 3, so that the medical instrument 4 is released for operation.

Figure 3:
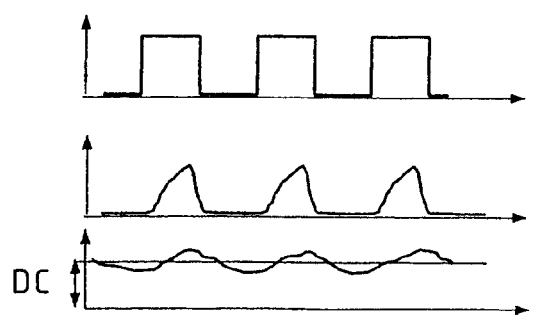
FIG. 3 shows a schematic view of the electrical voltage signals of the switching according to FIG. 2.

The structure of the capacity-sensitive electric current shown in exemplary manner in FIG. 2 includes a digital oscillator 9 for producing a wave-shaped electrical signal of known voltage, which fluctuates between a low and a high voltage as shown in the upper graph in FIG. 3.

The oscillator 9 is connected by a diode 10 with the touch-sensitive surface 11, which has a low internal capacitance. If the sensor 6 is not touched, the low capacity of the touch-sensitive surface 11 is quickly loaded with the signal with high voltage. On the other hand, the capacity of the touch-sensitive surface 11 in the phase of low oscillator voltage is quickly discharged by the resistance 12 to the earth 13. Under these conditions, the output signal of the sensor 6 is a wave, which oscillates with the same voltage as the oscillator 9 between high and low voltages, as shown in the center graph in FIG. 3.

If the surgeon 5 touches the touch-sensitive surface 11, the capacity of the human body, which is considerably greater than the capacity of the touch-sensitive surface 11, is added to the electric circuit. A value of about a 66 pF is cited in the literature for the capacity of the human body. The oscillator 9 charges this capacity during the signal phase with high voltage, but the diverting to earth 13 during the signal phase is low at reduced voltage, because the resistance 12 limits the current diversion. The result is that the voltage of the touch-sensitive surface 11 never sinks back to zero as long as the sensor 6 is touched. The output signal under these conditions is a fluctuating wave form with a firm direct current loading, as shown in the lower graph of FIG. 3. The touched condition of the touch-sensitive surface 11 can thus be distinguished from the untouched condition by the presence of this direct current supply.

To be able to distinguish between the two wave-shaped voltage signals of the touched and untouched condition at the output of the sensor 6, further electric circuits, not shown, must be added. These "distinguishing circuits" in turn can be used in order to provide electrical construction elements, which release or block the carrier arm 1 and the medical instrument 4.

Distinguishing between the two wave shapes can, for instance, be carried out by means of a simple logical switching. By compensating the value of the resistance 12 and the frequency of the oscillator 9 and adapting the "distinguishing circuits," the sensitivity of the entire system can be adjusted.

To ensure that the capacity of the patient 7 does not emerge as a disturbance capacity, it is essential to ensure that the patient 7 is permanently connected with the capacity-sensitive electric current and thus the capacity of the patient 7 is continually added to the capacity of the touch-sensitive surface 11. Conveying the patient's capacity into the system can proceed, for instance, by means of grounding pads known from electro-surgery.

The systems is then so adjusted that the capacities of the touch-sensitive surface 11 and of the patient 7 can be unloaded by means of the resistance 12 if the sensor 6 is not touched and the oscillator voltage is low. On the other hand, the direct current supply is added to the capacity of the surgeon 5 as soon as the surgeon 4 touches the sensor 6. In this way the system remains sensitive to touching by the surgeon 5, but insensitive to the capacity of the patient 7.

The invention claimed is:

1. A holding device for medical purposes having a carrier arm on whose distal end at least one medical instrument can be secured and having at least one joint for positioning the carrier arm and/or the medical instrument, so that the at least one joint can be transferred between a position that releases the at least one joint and a position that blocks the at least one joint and so that the at least one joint is coupled by means of a capacity-sensitive electrical circuit with a capacitive touch sensor to activate the at least one joint, wherein the medical instrument that is positioned on the distal end of the carrier arm is mounted in an adjustable instrument intake, wherein the instrument intake is coupled likewise with the touch sensor and wherein the touch sensor is coupled with the medical instrument that is mounted on the distal end of the carrier arm in such a way that on the one hand the at least one joint as well as the adjustable instrument intake are automatically released at the moment when the operator touches a touch sensitive surface of the medical instrument and on the other hand the at least one joint as well as the adjustable instrument intake are automatically locked at the moment when the operator releases the touch sensitive surface of the medical instrument.

* * * * *